United States Patent [19]

Naka

[11] Patent Number: 5,545,722
[45] Date of Patent: Aug. 13, 1996

[54] HEPATOCYTE-GROWTH AGENT

[75] Inventor: Daiji Naka, Yokohama, Japan

[73] Assignee: Mitsubishi Kasei Corporation, Tokyo, Japan

[21] Appl. No.: 292,051

[22] Filed: Aug. 19, 1994

Related U.S. Application Data

[63] Continuation of Ser. No. 892,180, Jun. 2, 1992, abandoned.

[30] Foreign Application Priority Data

| Jun. 3, 1991 | [JP] | Japan | 3-131271 |
| Feb. 25, 1992 | [JP] | Japan | 4-038122 |

[51] Int. Cl.$^6$ ............ A61K 38/24; A61K 38/27; A61K 31/715; A61K 31/725
[52] U.S. Cl. .......................... 530/399
[58] Field of Search .............. 530/399; 514/56, 514/54, 59

[56] References Cited

U.S. PATENT DOCUMENTS

| 5,004,805 | 4/1991 | Gohda et al. | 530/399 |
| 5,013,714 | 5/1991 | Lindstrom | 514/4 |

FOREIGN PATENT DOCUMENTS

| 0312208 | 4/1989 | European Pat. Off. |
| 0412577A1 | 2/1991 | European Pat. Off. |
| 0456188 | 11/1991 | European Pat. Off. |
| 047916 | 1/1990 | Japan |
| 02040399 | 2/1990 | Japan |

OTHER PUBLICATIONS

Mizuno, K. et al., "Cell Structure and Function." vol. 17 (6), 1992, p. 469, abstract #1A-/300.

Arakaki et al., "Identification and Partial Characterization of Two Classes of Receptors for Human Hepatocyte Growth Factor On Adult Rat Hepatocytes in Primary Culture," *J. Biol. Chem.* 267(10): 7101–7107 (1992).

Komada et al., "Characterization of hepatocyte–growth–factor receptors on Meth A cells," *Eur. J. Biochem.* 204: 857–864 (1992).

Roghani et al., "Basic Fibroblast Growth Factor Is Internalized through Both Receptor–mediated and Heparan Sulfate–mediated Mechanisms," *J. Biol. Chem.* 267(31): 22156–22162 (1992).

Zarnegar et al. "Purification and Biological Characterization of Human Hepatopoietin A, A Polypeptide Growth Factor For Hepatocytes", *Cancer Research* 49: 3314–3320 (1989).

Zarnegar et al."Identification and Partial Characterization of Receptor Binding Sites for HGF on Rat Hepatocytes", *Biochem. Research Communications* 173(3): 1179–1185 (1990).

Ruoslahtl et al. "Proteoglycans as Modulators of Growth Factor Activities", *Cell* 64: 867–869 (1991).

*Primary Examiner*—Michael G. Wityshyn
*Assistant Examiner*—Kristin Larson
*Attorney, Agent, or Firm*—Foley & Lardner

[57] ABSTRACT

Disclosed is a hepatocyte-growth agent which comprises a polysaccharide or a derivative such as heparin, heparan sulfate, chondroitin sulfate and dextran sulfate and a hepatocyte-growth factor (hHGF) obtained by purification of plasma or recombination, by which activity of the hHGF is strengthened, and an hHGF molecule is stabilized.

8 Claims, 6 Drawing Sheets

HEPATOCYTE-GROWTH AGENT

This application is a continuation application Ser. No. 07/892,180, filed Jun. 2, 1992, and now abandoned.

BACKGROUND OF THE INVENTION

This invention relates to a hepatocyte-growth agent which promotes growth of hepatocytes, more specifically to a hepatocyte-growth agent which comprises a polysaccharide or a derivative thereof and a hepatocyte-growth factor, in which said hepatocyte-growth factor is stabilized and further, its growth activity is heightened.

In recent years, a proteinaceous factor derived from humans, which can promote the growth of hepatocytes, namely, a human hepatocyte-growth factor (hereinafter sometimes abbreviated as "hHGF") has been found in the plasma of patients with fulminant hepatic failure (Japanese Provisional Patent Publication No. 22526/1988). Further, there has been a proposed amino acid sequence and a gene (cDNA) sequence which codes hHGF protein (Japanese Provisional Patent Publication No. 72883/1991), and a method for producing hHGF protein using this cDNA and a transformant thereof (Japanese Provisional Patent Publication No. 285693/1991). It has been recognized that hHGF has mitogenic activity for hepatocytes in vitro.

SUMMARY OF THE INVENTION

The present inventors have further studied the influences of a polysaccharide or a derivative thereof on hepatocyte-growth activity of hHGF. Namely, they have measured various influences on hepatocyte-growth activities (1) when a polysaccharide or a derivative thereof and the hHGF are mixed and added, (2) when a polysaccharide or a derivative thereof is added and then the hHGF is added, and (3) when the hHGF is added and then a polysaccharide or a derivative thereof is added to the hepatocytes prepared by Seglen's method (Methods in Cell Biology, vol. 13, p. 29, Academic Press, New York (1976)).

It was found for the first time, that the ability of promoting growth of hepatocytes possessed by hHGF is extremely strengthened when a polysaccharide or a derivative thereof and the hHGF are mixed and added, or when a polysaccharide or a derivative thereof is added and then hHGF is added. Additionally, degradation of the hHGF existing in a medium supernatant is suppressed by adding a polysaccharide or a derivative thereof to a system of measuring the growth of hepatocytes by the hHGF, namely, hHGF molecule is stabilized to accomplish the present invention.

The present invention resides in a hepatocyte-growth agent which comprises a polysaccharide or a derivative thereof and a hepatocyte-growth factor.

DESCRIPTION OF THE PREFERRED EMBODIMENTS

Figure 1:
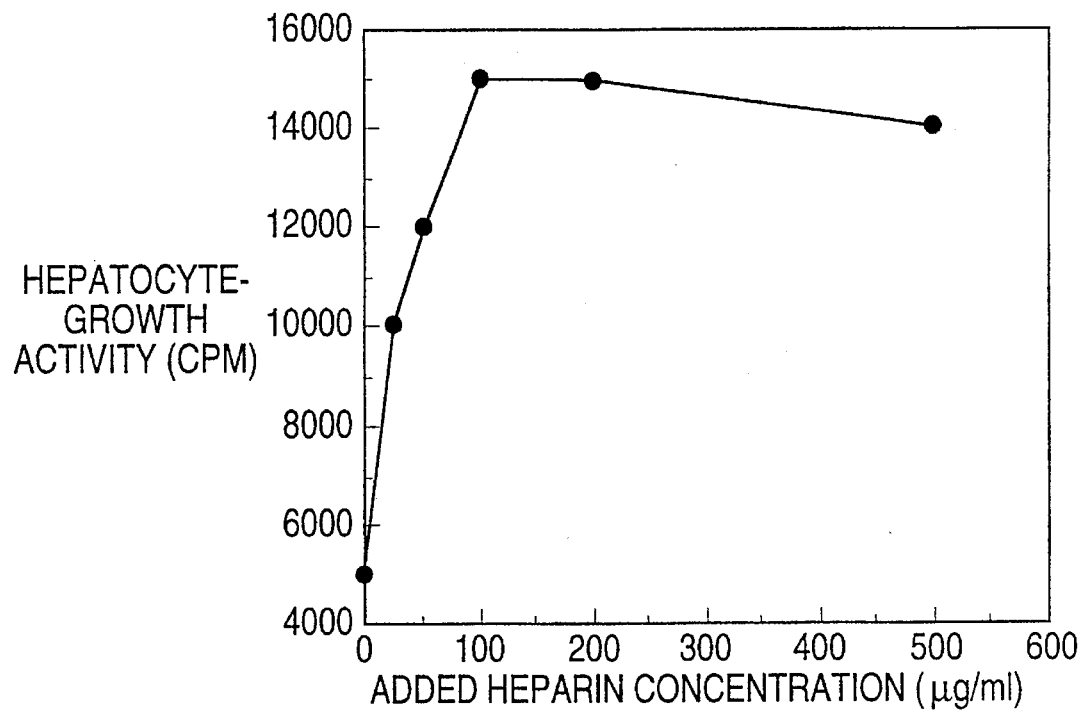
FIG. 1 is a diagram showing the relation between heparin concentration and hHGF activity when hHGF activity is heightened by adding heparin.

In the following, the present invention is explained in detail.

The hHGF to be used in the present invention is a proteinaceous factor derived from humans, having the activity of promoting growth of hepatocytes, being obtained either by purification from plasma or expression of cDNA. More specifically, hHGF can be obtained by separating and purifying proteinaceous factors chemically from the plasma of patients with fulminant hepatic failure and purifying it according to the method disclosed in Japanese Provisional Patent Publication No. 22526/1988. hHGF may also be obtained by constituting an expression vector containing cDNA which codes the hHGF obtained from the cDNA library derived from human placenta and expresses it in a host such as a CHO cell according to the method disclosed in Japanese Provisional Patent Publication No. 285693/1991.

Such a hHGF is a heterodimeric protein in which a large sub-unit with a molecular weight of about 56,000 to 65,000 daltons and a small sub-unit with a molecular weight of about 32,000 to 35,000 daltons are linked by a disulfide bond, having a band molecular weight of about 76,000 to 92,000 daltons by SDS-PAGE under non-reducing conditions and gives main band molecular weights of about 56,000 to 65,000 daltons and about 32,000 to 35,000 daltons by SDS-PAGE under reducing conditions. This hHGF loses its activity of promoting growth of hepatocyte by heat treatment at 80° C. for 10 minutes or trypsin or chymotrypsin digestion and shows strong affinity for heparin. In general, the hHGF to be used in the present invention begins to exhibit a hepatocyte-growth activity at a concentration of about 0.5 to 2 ng/ml and exhibits a good growth activity at a concentration of about 5 to 10 ng/ml.

In the present invention, hHGF and a polysaccharide or a derivative thereof are used in combination. The polysaccharide or a derivative thereof herein mentioned in the present invention means a carbohydrate formed by dehydration and condensation of at least two monosaccharides through glycoside linkage, i.e., includes all glycans or a derivative thereof. Such a polysaccharide or a derivative thereof may have a structure in which disaccharide units are repeated, as in glycosaminoglycan, and suitably used are those in which one of the disaccharides comprises glucosamine or galactosamine (Science of Life, 39 (4), pp. 306 to 310 (1988)) or a derivative in which a polysaccharide such as glucan is sulfated. More specifically, for example, hyaluronic acid, chondroitin, chondroitin sulfate, dermatan sulfate, heparan sulfate, keratan sulfate, heparin, dextran and dextran sulfate may be used. Preferably used is a sulfate derivative of a polysaccharide such as heparin, dextran sulfate, heparan sulfate and chondroitin sulfate.

The polysaccharide or a derivative thereof is preferably used in an excessive amount based on the amount of the hHGF and is generally used in the range of $10^2$ to $10^5$ mole per mole of the hHGF.

The hepatocyte-growth agent of the present invention is mainly used as an injection. The injection may be prepared according to a conventional method. In that case, a known additive such as human serum albumin and a surfactant may be used in combination. More specifically, for example, it may be prepared by dissolving any of the compositions shown below in a 10 mM phosphate buffer solution (PBS(–)) having a pH of 7.5, making the total amount of the mixture up to 5 ml, sterilizing it by a filter of 0.22 μm and apportioning it to vials or further lyophilizing and storing the mixture and suitably dissolving it in distilled water or physiological saline when it is used.

(1) 100 μg of hHGF, 50 mg of human serum albumin and 0.5 mg of the non-ionic detergent TRITON X-100 (trade name, produced by, e.g. NACALAI TESQUE, INC.)

(2) 100 μg of hHGF and 50 mg of human serum albumin (3) 100 μg of hHGF and 0.5 mg of the non-ionic detergent TRITON X-100 (supra)

(4) 100 μg of hHGF and 0.5 mg of the non-ionic detergent TWEEN 80 (trade name, produced by, e.g. NACALAI TESQUE, INC.)

(5) 5 mg of heparin (6) 5 mg of heparin, 50 mg of human serum albumin and 0.5 mg of the non-ionic detergent TRITON X-100 (supra)

(7) 100 μg of hHGF, 5 mg of heparin, 50 mg of human serum albumin and 0.5 mg of the non-ionic detergent TRITON X-100 (supra)

(8) 100 μg of hHGF, 5 mg of heparin and 50 mg of human serum albumin (9) 100 μg of hHGF, 5 mg of heparin and 0.5 mg of the non-ionic detergent TRITON X-100 (supra)

(10) 100 μg of hHGF, 5 mg of heparin and 0.5 mg of the non-ionic detergent TWEEN 80 (supra)

(11) 100 μg of hHGF and 5 mg of heparin

In the present invention, an injection containing both the hHGF and the polysaccharide or a derivative thereof may be prepared and used. Otherwise, injections containing each of them are prepared, respectively, and after an injection containing the polysaccharide or a derivative thereof is used, an injection containing the hHGF may be used or both injections may be used simultaneously. When the injection containing the hHGF is used in advance, the injection containing the polysaccharide or a derivative thereof should be used immediately in succession.

The amount of the hepatocyte-growth agent of the present invention to be added varies depending on activity of the hHGF which is an active ingredient and a patient to which it is administered, but may be selected from the range of about 0.1 μg/kg to 1,000 μg/kg.

EXAMPLES

The present invention is described in detail by the following Examples, but is not limited to the following Examples so long as it falls within the scope of the invention.

Example 1

Heightening activation of hHGF protein by adding heparin

According to the Seglen's method (Methods in Cellbiology, vol. 13, p. 29, Academic Press, New York (1976)), hepatocytes were isolated from Wistar strain male rats (body weight: 200 g) by using 0.05% collagenase (TYPE I, trade name, produced by Sigma Co.). The hepatocytes were plated in collagen-coated multiwell plastic dishes (produced by Nunc) having wells with a diameter of 1.55 cm at a density of $5\times10^4/0.2$ ml/cm$^2$, and single layer culture was carried out at 37° C. under a gas phase of air containing 5% carbonic acid gas (Tanaka et al., J. Biochem. 84, pp. 937 to 946 (1978)). As a medium for the culture, Williams E medium, was used produced by Flow Laboratories, Co., hereinafter abbreviated as "basic medium"), to which 5% fetal bovine serum (FBS, produced by Filtron in Altona, Australia), 1 μM dexamethasone, 100 U/ml of penicillin and 100 μg/ml of streptomycin were added.

Three hours after initiation of the culture, the medium was exchanged with a new basic medium, and after 20 hours, the basic medium was exchanged with a basic medium containing no bovine fetal serum. After exchanging the mediums, when heparin (molecular weight: 4,000 to 6,000 daltons, produced by Sigma Co.) was added the final concentrations became 0, 50, 100, 200 and 500 μg/ml, respectively, and when a recombinant hHGF was added, the final concentration became 100 ng/ml. After culture was continued for 20 hours, DNA synthesis was measured. The DNA synthesis was examined by adding $^3$H-thymidine (produced by Amersham Co.) so that the final concentration became 4 μCi/ml (2 Ci/mmole), then continuing culture for 4 hours and measuring the uptake of $^3$H-thymidine to DNA. A group to which the hHGF was not added was used as a control group. After labeling with the above culture, the cells were washed three times with ice-cold PBS (–), then washed three times with 2% perchloric acid solution. Thereafter, the cells were further washed three times with 95% ethanol. Subsequently, the cells were air-dried and solubilized with 500 μl of 1N NaOH. Then, a part thereof was taken out, and the radioactivity was measured. A concentration of the recombinant hHGF was measured by an enzyme immunoassay. An activity value was determined as the difference between the uptake amount of $^3$H-thymidine to the hepatocyte DNA a sample tested and that of the control group. Herein, all activity values of hHGFs were determined by this method. The results are shown in FIG. 1. In FIG. 1, the axis of abscissas shows a final concentration of heparin, and the axis of ordinates shows an hHGF activity.

Figure 2:
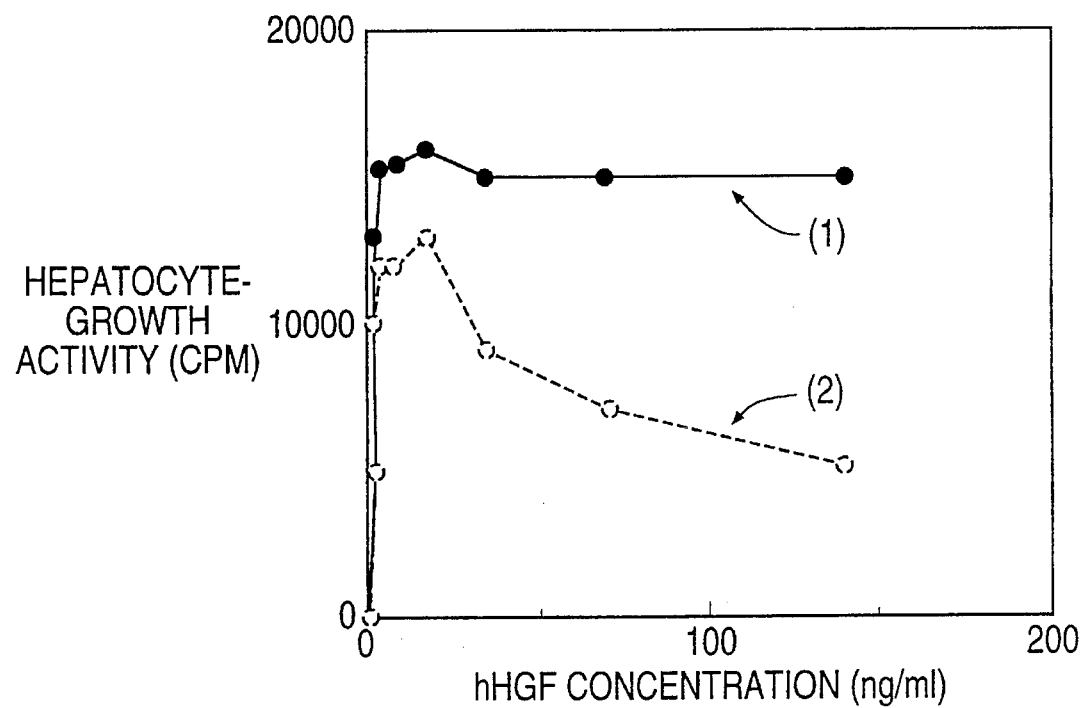
FIG. 2 is a diagram showing the relation between an hHGF concentration and hHGF activity when hHGF activity is heightened by adding a predetermined amount of heparin.

FIG. 2 shows results that when heparin (molecular weight: 4,000 to 6,000 daltons) was added, the final concentration became 100 μg/ml, and when the recombinant hHGF was added, the final concentrations became 0, 4.28, 8.75, 17.5, 35, 70 and 140 ng/ml, respectively. The axis of abscissas shows the final concentration of the recombinant hHGF when heparin was added, and the axis of ordinates shows the hHGF activity. In FIG. 2, curve (1) shows the hHGF activity when heparin was added, and the final concentration became 100 μg/ml, and curve (2) shows the hHGF activity when heparin was not added.

From the results in FIG. 1 and FIG. 2, it can be seen that activity of hHGF protein is heightened by adding heparin.

Example 2

Inhibition of hHGF protein degradation by adding heparin

According to the Seglen's method (Methods in Cellbiology, vol. 13, p. 29, Academic Press, New York (1976)) shown in Example 1, hepatocytes were separated. The hepatocytes were plated in collagen-coated, multiwell plastic dishes (produced by Nunc) having wells with a diameter of 3.5 cm at a density of $5 \times 10^4/0.2$ ml/cm$^2$. Thereafter, single layer culture was carried out at 37° C. under a gas phase of air containing 5% carbonic acid gas (Tanaka et al., J. Biochem. 84, pp. 937 to 946 (1978)). As a medium for the culture, Williams E medium was used (produced by Flow Laboratories, Co., hereinafter abbreviated as "basic medium") to which 5% fetal bovine serum (FBS, produced by Filtron in Altona, Australia), 1 µM dexamethasone, 100 U/ml of penicillin and 100 µg/ml of streptomycin were added.

Three hours after initiation of the culture, the medium was exchanged with a new basic medium, and after 20 hours, the basic medium was washed with PBS(–), containing 0.25% gelatin, three times. Then, 2 ml of Dulbecco's MEM (hereinafter abbreviated as "Binding medium", containing 0.25% gelatin and 25 mM hepes, was added into each well. Thereafter, single layer culture was carried out at 37° C. for 3 hours under gas phase of gas containing 5% carbonic acid gas. Subsequently, the Binding medium was exchanged and 1 ml of the Binding medium was added into each well. Further, when heparin (molecular weight: 4,000 to 6,000 daltons produced by Sigma Co.) was added, the final concentration became 100 µg/ml. A group to which heparin was not added was used as a control group. On the other hand, according to the Hunter et al method (Nature 194, pp. 495 and 496 (1962)), the recombinant hHGF was labeled by using a carrier-free Na$^{125}$I (3.7 GBQ, trade name, produced by NEN Co.). When the labeled hHGF obtained (hereinafter abbreviated to as "labeled hHGF") was added into each well, the final concentration became 200 pM. Thereafter, single layer culture was carried out at 37° C. under a gas phase of air containing 5% carbonic acid gas. A culture supernatant was collected at 0 minute, 10 minutes, 30 minutes, 60 minutes, 120 minutes and 180 minutes after initiation of the culture, and consequently chilled in ice. Subsequently, transfer-RNA was added and the final concentration became 100 µg/ml. Next, trichloroacetic acid (TCA) was added, the final concentration became 10%. The prepared sample to be tested was incubated for 3 hours under ice-cooling. Centrifugation of 10,000 G was carried out to collect a supernatant which was used for measuring the amount of the degraded hHGF. The supernatant thus obtained contained labeled hHGF having a lower molecular weight because of degradation caused by incubation with hepatocytes.

Figure 3:
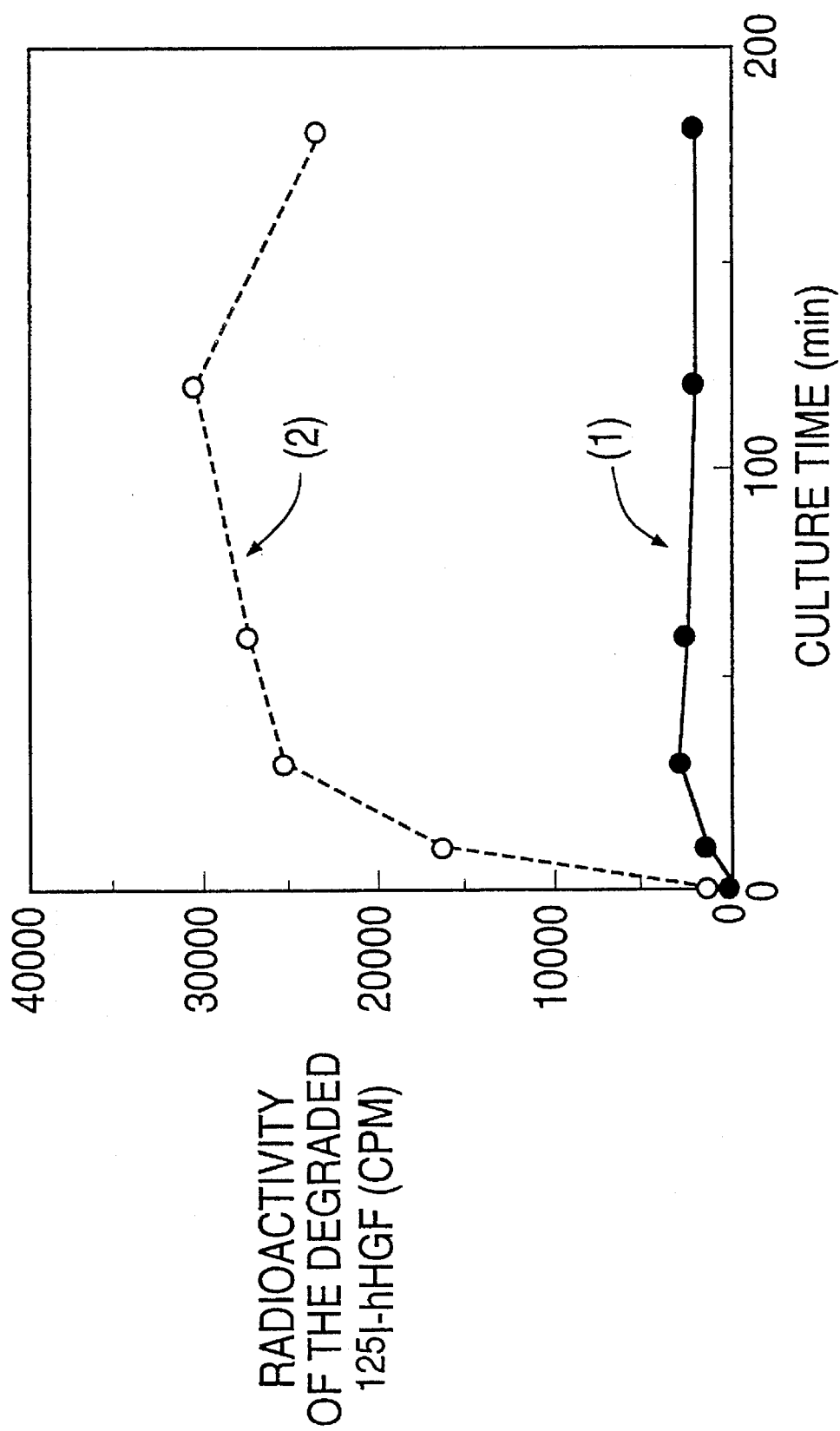
FIG. 3 is a diagram showing inhibition of a labeled hHGF degradation when a predetermined amount of heparin is added.

The results are shown in FIG. 3. The axis of abscissas shows time from addition of the labeled hHGF to the hepatocytes, to collection of the culture supernatant, and the axis of ordinates shows radioactivity of the degraded labeled hHGF. In FIG. 3, curve (1) shows the amount of the degraded labeled hHGF when heparin was added and the final concentration became 100 µg/ml, and curve (2) shows the amount of the degraded labeled hHGF when heparin was not added.

From the results in FIG. 3, it can be understood that degradation of hHGF protein is inhibited effectively by adding heparin.

Example 3

Hightening of hHGF protein by adding dextran sulfate and dextran Applicant examined the influence of dextran sulfate, having a molecular structure similar to that of heparin, and the influence of dextran having no sulfuric acid group in its molecule, on hepatocyte-growth activity possessed by hHGF.

In the same manner shown in Example 1, hepatocytes were isolated and cultured.

Three hours after initiation of the culture, the medium was exchanged with a new basic medium, and after 20 hours, the basic medium was exchanged with a basic medium containing the recombinant hHGF having a final concentration of 200 ng/ml and 1, 10, 50, 100 or 500 µg/ml of dextran sulfate (molecular weight: 8,000 daltons, produced by Sigma Co.), dextran (molecular weight: 10,000 daltons, produced by Sigma Co.) or heparin (molecular weight: 4,000 to 6,000 daltons, produced by Sigma Co.) and containing no fetal bovine serum. After the culture was continued for 20 hours, synthesis of DNA was measured. The synthesis of DNA and the concentration of the recombinant hHGF were measured in the same manner as in Example 1.

Figure 4:
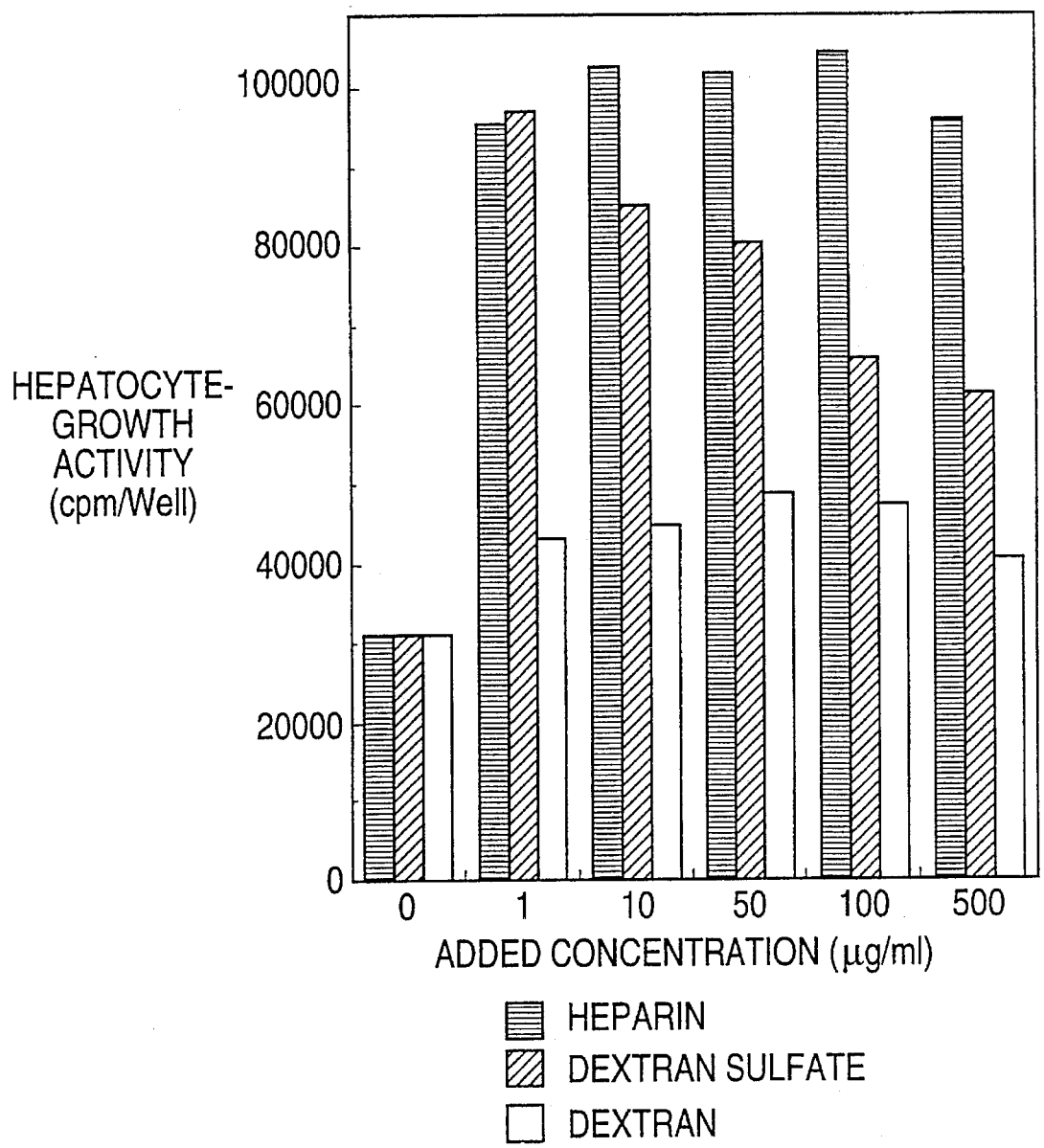
FIG. 4 is a diagram showing hepatocyte-growth activity of a hHGF when various concentrations of dextran sulfate, dextran and heparin are added to a predetermined amount of hHGF.

The results are shown in FIG. 4. In FIG. 4, the axis of abscissas shows a final concentration of dextran sulfate, dextran or heparin added, and the axis of ordinates shows activity of the hHGF.

As shown in FIG. 4, a hepatocyte-growth activity possessed by the hHGF can be strengthened even by adding dextran sulfate or dextran. Particularly, it can be seen that dextran sulfate significantly strengthens activity of the hHGF, similar to heparin.

Example 4

Heightening activation of hHGF protein by adding various polysaccharide and derivatives thereof The influences of heparin, dextran sulfate and dextran used in the examples described above, as well as heparin sulfate, hyaluronic acid, chondroitin and chondroitin sulfates A to E which were used as samples to be tested, on hepatocyte-growth activity possessed by hHGF were examined.

In the same manner as in Example 1, hepatocytes were isolated. Also in the same manner as in Example 1, these hepatocytes were plated in collagen-coated multiwell plastic dishes (produced by Nunc) having wells with a diameter of 1.55 cm at a density of $5 \times 10^4/0.2$ ml/cm$^2$. Thereafter single layer cultivation was carried out at 37° C. under a gas phase of air containing 5% carbonic acid gas. As a medium for the culture, Williams E medium was used (produced by Flow Laboratories, Co., hereinafter abbreviated to as "basic medium") to which 5% fetal bovine serum (FBS, produced by Filtron in Altona, Australia), 1 µM dexamethasone, 100 U/ml of penicillin and 100 µg/ml of streptomycin were added. Three hours after initiation of the culture, the medium was exchanged with a basic medium, and after 20 hours, the basic medium was exchanged with a basic medium containing no fetal bovine serum.

Subsequently, each sample to be tested and a recombinant hHGF were mixed with equal volume to obtain a mixture containing 100 µg/ml of the sample and 200 ng/ml of the recombinant hHGF. After culture was continued for 20 hours, DNA synthesis of hepatocytes was measured. The DNA synthesis was examined by the same method described in Example 1. A group to which the hHGF was not added was used as a control group. After labeling with the above culture, the cells were washed three times with ice-cold PBS (–), then washed three times with 2% perchloric acid solution. Thereafter, the cells were further washed three times with 95% ethanol. Subsequently, the cells were air-dried and solubilized with 500 μl of 1N NaOH. A part thereof was taken out, and radioactivity was measured. A concentration of the recombinant hHGF was measured by enzyme immunoassay. An activity value was determined as the difference between the uptake amount of $^3$H-thymidine to hepatocyte DNA and that of the control group. The results are shown in FIG. 5.

Figure 5:
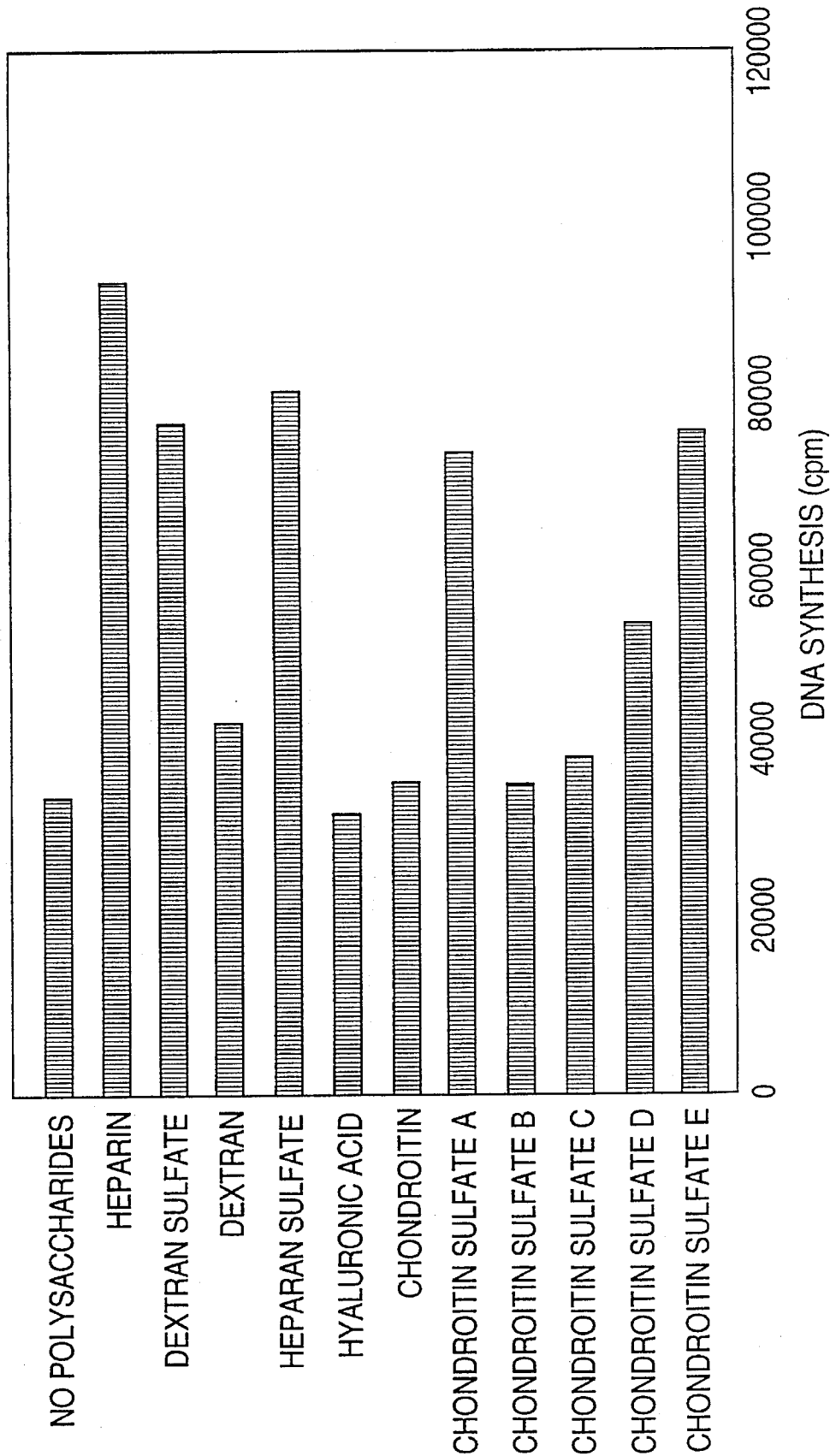
FIG. 5 is a diagram showing hepatocyte-growth activity of hHGF when various polysaccharides and derivatives thereof are added to a predetermined amount of the hHGF.

In FIG. 5, the axis of ordinate shows various polysaccharides, glycosaminoglycan and derivatives thereof, and the axis of abscissa shows hHGF activities. It is shown that hHGF activities were remarkably heightened by adding heparin, dextran sulfate, heparan sulfate and chondroitin sulfate A, D and E.

Example 5

Preparation of polysaccharide- or derivative thereof-bound type hHGF protein and strengthening of hepatocyte-growth activity thereof.

The hHGF has strong affinity for a polysaccharide heparin and dextran sulfate, or a derivative thereof. Therefore, a polysaccharide- or derivative thereof-bound type hHGF only was prepared by mixing the polysaccharide or a derivative thereof with the hHGF and removing the polysaccharide or a derivative thereof which was not bound to the hHGF. It is particularly known that heparin and dextran sulfate exhibit an anticoagulant effect on blood in vivo. However, it can be expected that the influences of a simple polysaccharide or a derivative thereof (for example, heparin or dextran sulfates which are not bound to a hHGF), on living bodies are extremely suppressed by using the present method. Further, it can be seen that the hHGF to which such molecule is bound induces extremely strong a hepatocyte-growth activity, as similar to the activity shown in Example 1, a compared with the case when only the hHGF is added.

In the following, a method for preparing polysaccharide- or derivative thereof-bound type hHGF protein and strengthening hepatocyte-growth activity thereof are described.

To 1 ml of a PBS(–) solution containing 1 mg of the recombinant hHGF protein was added 100 μl of a PBS(–) solution containing heparin (molecular weight: 4,000 to 6,000 daltons produced by Sigma Co.) so as to have a final concentration of 50 mg/ml. After the mixture was incubated at 4° C. for 24 hours, heparin, which was not bound to the hHGF, was removed by a gel filtration procedure using a SEPHADEX G-50 column (manufactured by Pharmacia Co.). Namely, after the SEPHADEX G-50 column (manufactured by Pharmacia Co.) (1.5×12 cm) equilibrated with a PBS(–) solution (hereinafter abbreviated to as "eluting buffer solution") containing a final concentration of 0.01% of the non-ionic detergent TWEEN 80 produced by NACALAI TESQUE, INC.) was charged with a mixture of heparin and the hHGF, the column was charged with the eluting buffer solution. The hHGF protein (hereinafter abbreviated as "heparin-bound type hHGF", to which heparin was bound, was collected in a void volume fraction of the same column. [On the other hand, since the heparin (produced by Sigma Co.) used in the present procedure has a low molecular weight of 4,000 to 6,000 daltons, it was not eluted in the void volume fraction in which the heparin-bound type hHGF was collected].

Next, the hepatocyte-growth activity of the heparin-bound type hHGF was measured.

In the same manner shown in Example 1, hepatocytes were isolated and cultured. Three hours after initiation of the culture, the medium was exchanged with a basic medium, and after 20 hours, the basic medium was exchanged with a basic medium containing no bovine fetal serum (produced by Flow Laboratories Co.). After this exchange of the medium, the heparin-bound type hHGF having a final concentration of 0, 0.5, 2, 10, 50, 100 or 300 μg/ml, or the hHGF to which heparin was not bound, was added as the sample to be tested. After culture was continued for 24 or 48 hours, synthesis of DNA was measured. The synthesis of DNA was examined by adding $^3$H-thymidine (produced by Amersham Co.) so that the final concentration became 4 μCi/ml (2 Ci/mmole), continuing culture at 37° C. for 5 hours and measuring uptake of $^3$H-thymidine to DNA. A group to which the hHGF was not added was used a control group. After labeling with the above culture, the cells were washed three times with ice-cold PBS (–), then washed three times with 2% perchloric acid solution. Thereafter, the cells were further washed three times with 95% ethanol. Subsequently, the cells were air-dried and solubilized with 500 μl of 1N NaOH. Then, a part thereof was taken out, and the radioactivity was measured. The concentrations of the recombinant hHGF and the heparin-bound type hHGF were measured by the enzyme immunoassay in the same manner as in Example 1. The activity value was determined as the difference between the uptake amount of $^3$H-thymidine to hepatocyte DNA and that of the control group.

Figure 6:
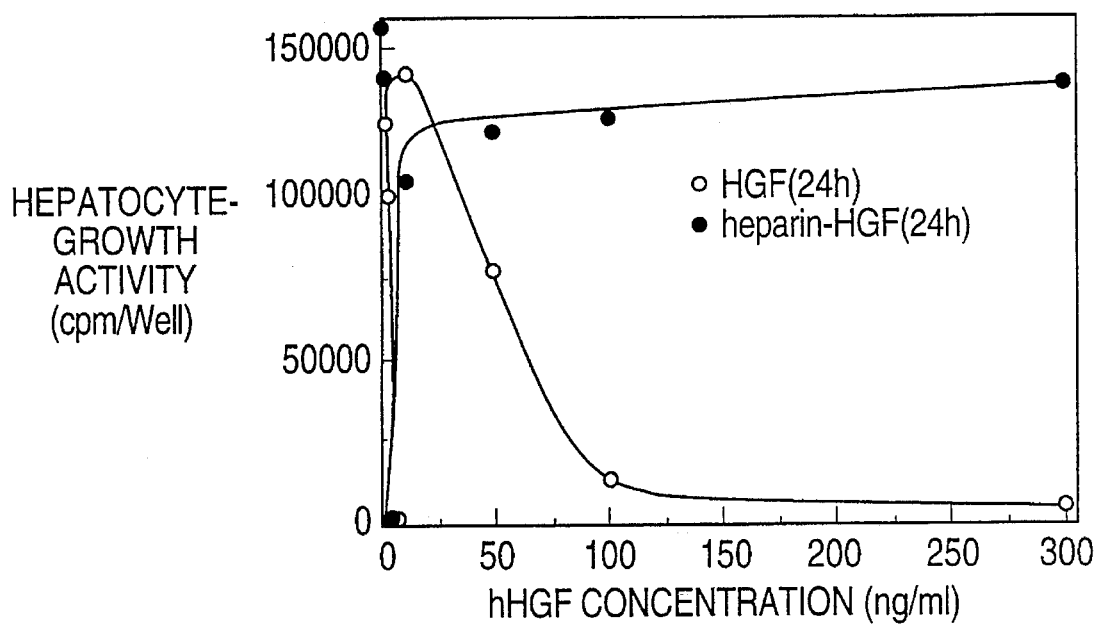
FIG. 6 is a diagram showing results of relations between concentrations of a heparin-bound type hHGF and a hHGF to which heparin is not bound, and hepatocyte-growth activities, when cultivation was carried out for 24 hours after addition of each sample to be tested.
Figure 7:
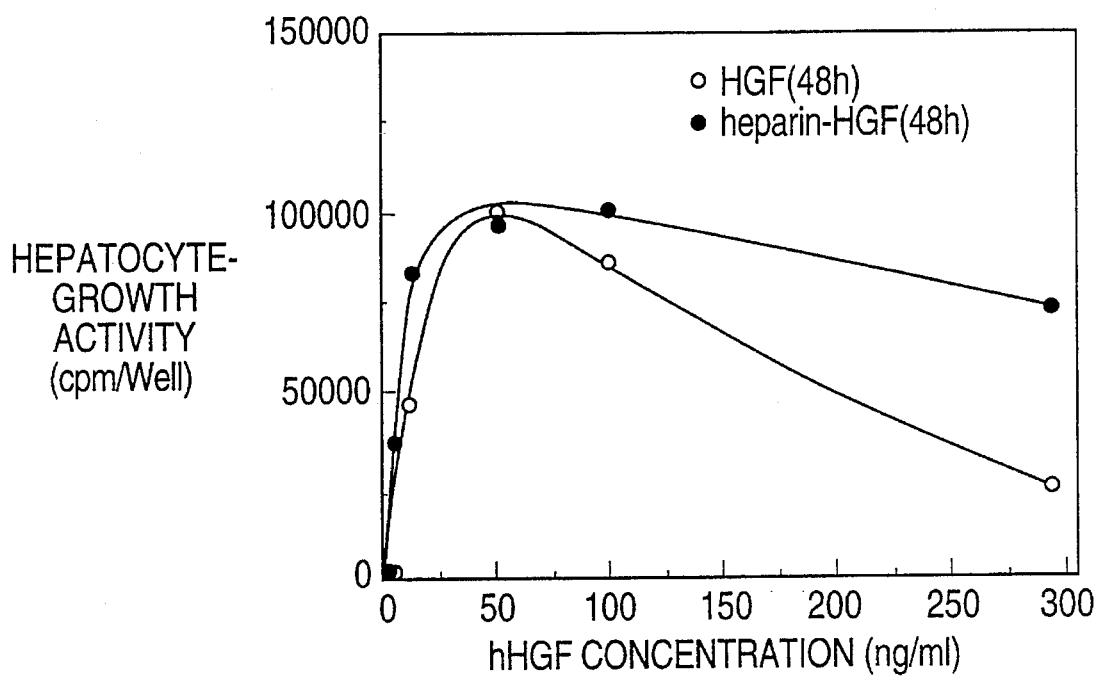
FIG. 7 is a diagram showing results of relations between concentrations of a heparin-bound type hHGF and a hHGF to which heparin is not bound, and hepatocyte-growth activities, when cultivation was carried out for 48 hours after addition of each sample to be tested.

After adding the samples to be tested, cultivation was carried out for 24 hours, as shown in FIG. 6 and for 48 hours, as shown in FIG. 7. In FIG. 6 and FIG. 7, the axes of abscissas show final concentrations of heparin, and the axes of ordinates show activities of the hHGF.

As shown in FIG. 6 and FIG. 7, it can be observed that the heparin-bound type hHGF strengthens and maintains a high hepatocyte-growth activity by adding it in amounts ranging from low concentration to high concentration, as compared with the hHGF to which heparin is not bound. It can be particularly seen that the heparin-bound type hHGF maintains a stable high activity while the hHGF to which heparin is not bound extremely decreases in hepatocyte-growth activity when added at a concentration of 50 to 300 ng/ml.

Example 6

Various preparations of polysaccharides- and derivatives thereof-bound type hHGF proteins and inhibition of the hHGF protein-degradation In the same manner as in Example 2, according to the Hunter et al. method, a recombinant hHGF was labeled by using Na$^{125}$I (3.7 GBQ, produced by NEN Co.). To 200 μl of a PBS(–) solution containing 3 μg of the labeled recombinant hHGF protein obtained was added 200 μl of a PBS(–) solution containing heparin (molecular weight: 4,000 to 6,000 daltons, produced by Sigma Co.) or dextran sulfate (molecular weight: 8,000 daltons, produced by Sigma Co.), so as to have a final concentration of 50 mg/ml. After the mixture was incubated at 4° C. for 24 hours, heparin or dextran sulfate which was not bound to the hHGF was removed by gel filtration procedure using a SEPHADEX G-50 column (manufactured by Pharmacia Co.). Namely, the SEPHADEX G-50 column (manufactured by Pharmacia Co.) (1.5×12 cm) was equilibrated with a PBS(–) solution containing a final concentration of 0.01% of the non-ionic detergent TWEEN 80 (produced by NACALAI TESQUE, INC.) (hereinafter abbreviated to as "eluting buffer solution"). The column was charged with a mixture of heparin or dextran sulfate and the hHGF, which were eluted with the eluting buffer solution. The labeled hHGF protein (hereinafter abbreviated as "heparin-bound type $^{125}$I-hHGF" or "dextran sulfate-bound type $^{125}$I-hHGF"), which was bound to heparin or dextran sulfate molecules, was collected in void volume fraction of the same column.

Next, hepatocytes were prepared in the same manner shown in Example 2.

That is, according to the Seglen method, hepatocytes were plated in collagen-coated multiwell plastic dishes (produced by Nunc) having wells with a diameter of 3.5 cm at a density of $5 \times 10^4/0.2$ ml/cm$^2$, and single layer culture was carried out at 37° C. under a gas phase of air containing 5% carbonic acid gas. As a medium for the culture, Williams E medium was used (produced by Flow Laboratories, Co., hereinafter abbreviated to as "basic medium,") to which 5% fetal bovine serum (FBS, produced by Filtron in Altona, Australia), 1 μM dexamethasone, 100 U/ml of penicillin and 100 μg/ml of streptomycin were added Three hours after initiation of the culture, the medium was exchanged with a basic medium, and after 20 hours, the basic medium was washed with PBS(–) containing 0.25% gelatin three times. Then, 2 ml of the above Binding medium was added to each well, and single layer culture was carried out at 37° C. for 3 hours under a gas phase of air containing 5% carbonic acid gas. Thereafter, the Binding medium was exchanged with 1 ml of a Binding medium which was added to each well.

When heparin-bound type $^{125}$I-hHGF or dextran sulfate-bound type $^{125}$I-hHGF was added to the hepatocytes prepared, the final concentration became 200 pM. A group of only $^{125}$I-hHGF was used as a control group.

Then, single layer culture was carried out at 37° C. under a gas phase of air containing 5% carbonic acid gas. A culture supernatant was collected at 0 minute, 10 minutes, 30 minutes, 60 minutes, 120 minutes, 180 minutes and 360 minutes after initiation of the culture, and the culture supernatant collected was sufficiently chilled in ice. Subsequently, when transfer RNA was added, the final concentration became 100 μg/ml, and when trichloroacetic acid (TCA) was added, the final concentration became 10%. Each sample prepared was incubated for 3 hours under ice-cooling, and then centrifugation of 10,000 G was carried out at 4° C. to collect a supernatant and a precipitating fraction. In the supernatant thus obtained (hereinafter referred to "TCA-solubilizing fraction"), the labeled hHGF of which a molecular weight was made lower, namely degraded by incubation with hepatocytes, was contained. On the other hand, in the precipitating fraction (hereinafter referred to "TCA-precipitating fraction"), the hHGF which was not degraded, was contained. Radioactivities of the TCA-solubilizing fraction and TCA-precipitating fraction obtained were measured to calculate a ratio thereof.

Figure 8C:
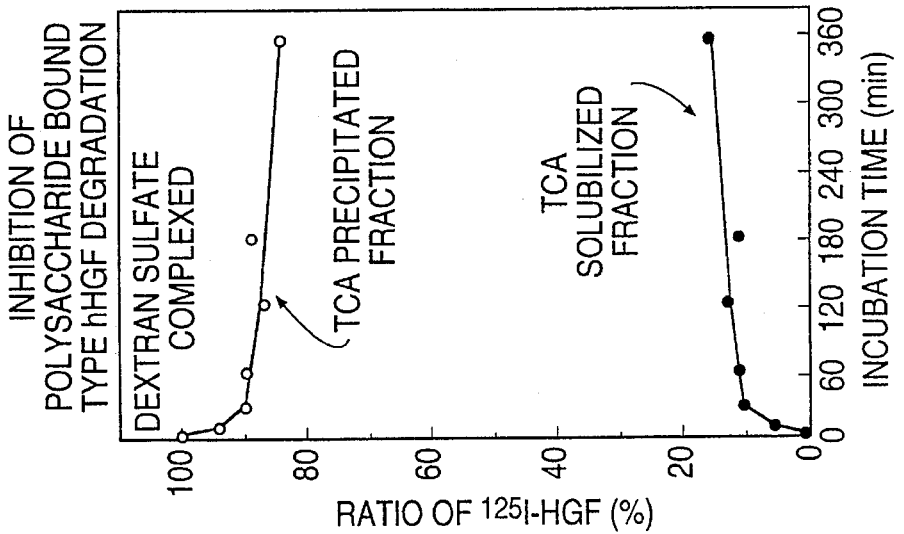
FIG. 8 is a diagram showing inhibition of degradation of a heparin-bound type hHGF and dextran sulfate-bound type hHGF.
Figure 8B:
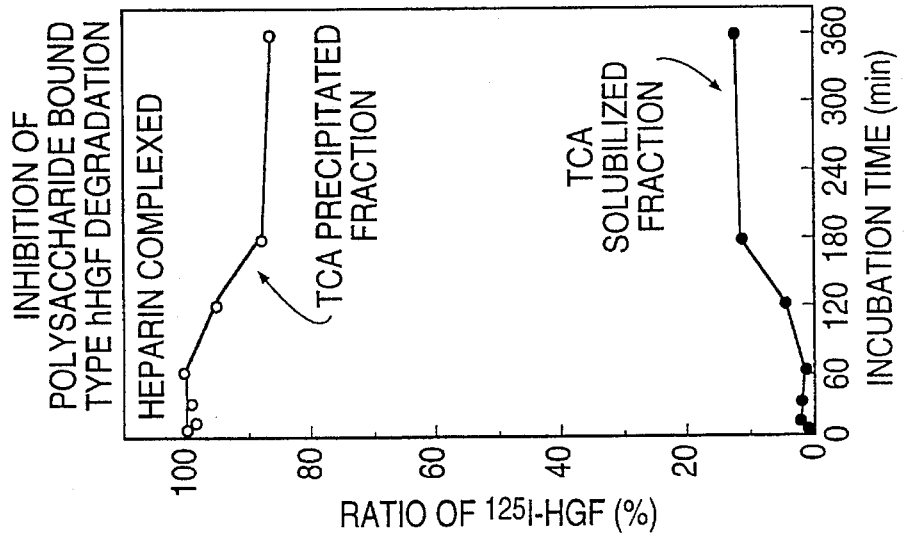
Figure 8A:
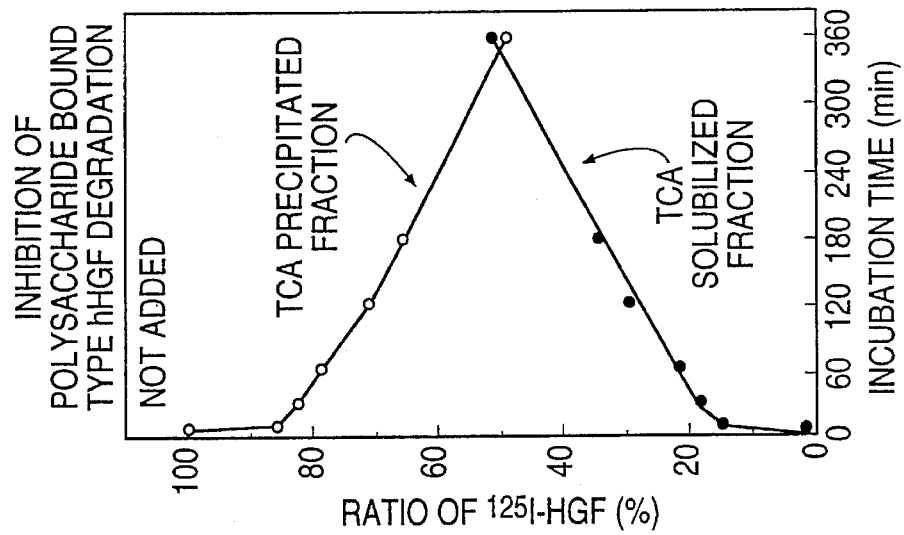

The results are shown in FIG. 8. FIG. 8(A) shows a case when only $^{125}$I-hHGF was added; FIG. 8(B) a case when the heparin-bound type $^{125}$I-hHGF was added; and FIG. 8(C) a case when the dextran sulfate-bound type $^{125}$I-hHGF. The axis of abscissas shows the time from addition of the sample to be tested to hepatocytes to the collection of the culture supernatant, and the axis of ordinate shows a ratio of radioactivity of the TCA-solubilizing fraction and the TCA-precipitating fraction to the total radioactivity.

As shown in FIG. 8(B) and FIG. 8(C), degradation of hHGF molecules which are bound to heparin or dextran sulfate are inhibited extremely by adding heparin-bound type or dextran sulfate-bound type hHGF.

Example 7

Promotion of liver regeneration in rats by hHGF to which heparin is added

After an operation for excising ⅔ of livers of rats (body weight: about 200 g) under anesthesia was carried out, an osmotic pressure pump, ALZET 2001 (produced by ALZET), filled with 200 μl of a sample solution to be tested and previously stored at 37° C. overnight was cannulated to cervical veins, and the sample solution to be tested was continuously fed into venous blood at a rate of 1 μl per hour. After 5 days, the rats were killed, and the liver weights were measured.

The sample solution to be tested was a buffer solution with a pH of 7.5 containing 10 mM sodium phosphate and 0.7M sodium chloride. As the sample solution to be tested, a solution containing 0.8 μg/ml of the recombinant hHGF was used in the hHGF-administered group (6 rats), and a solution containing 5 μg/ml of heparin (molecular weight: 4,000 to 6,000 daltons, produced by Sigma Co.) in addition to the recombinant hHGF was used in the hHGF.heparin-administered group (5 rats). The buffer solution-administered group (6 rats) was designated as a control group.

As shown in Table 1, the liver regeneration rate of the hHGF-administered group was significantly higher ($P<0.05$) than that of the buffer solution-administered group, and the rate of the hHGF.heparin-administered group was significantly higher ($P<0.05$) than that of the hHGF-administered group. Thus, it can be understood that heparin promotes action of the hHGF even in growth of hepatocyte in animal bodies. The liver regeneration rate was calculated according to the following formula:

Regeneration rate =

$$\frac{\text{Total weight of regenerated liver} - \left( \text{Weight of liver estimated} - \text{Weight of excised liver} \right)}{\text{Weight of excised liver}}$$

Weight of liver estimated =

Body weight × Ratio of liver weight to body weight*

*Ratio of liver weight to body weight of rat which underwent a false operation (only celiotomy without excising liver) after 5 days (0.0431 in the present Example)

TABLE 1

| Sample solution to be tested | Liver regeneration rate (%) |
|---|---|
| Buffer solution | 88.9 ± 5.3 |
| hHGF | 108.8 ± 4.2 |
| hHGF · heparin | 124.6 ± 5.5 |

In the prior art, there have not been known existence of a factor of highly activating or highly stabilizing such a protein for utilizing a hHGF industrially, and a method of utilization thereof.

As shown in the present invention, by using a polysaccharide or a derivative thereof and a hHGF in combination, activity of the hHGF is strengthened, and stability of a hHGF molecule is improved. As a result, effects of the hHGF on liver regeneration in the case of liver disorders in vivo can be further improved. Also, by using a polysaccharide or a derivative thereof according to the present invention, storage stability of a hHGF preparation can be expected.

I claim:

1. A hepatocyte growth-stimulating agent which comprises a sulfated polysaccharide and a hepatocyte-growth factor, wherein said hepatocyte-growth factor targets hepatocyte cells in vivo, wherein said sulfated polysaccharide improves the growth activity of said hepatocyte growth factor and wherein said agent is in an injectable form that can be administered in vivo to stimulate hepatocyte growth.

2. The agent according to claim 1, wherein the sulfated polysaccharide is glycosaminoglycan.

3. The agent according to claim 1, wherein the sulfated polysaccharide is bound to said hepatocyte-growth factor.

4. The agent according to claim 1, wherein said sulfated polysaccharide is present in an amount that is greater than the amount of said hHGF, wherein said amount is in a range of $10^2$ to $10^5$ mole per mole of hHGF and wherein said agent is soluble in a liquid carrier.

5. The hepatocyte growth-stimulating agent of claim 1, wherein said sulfated polysaccharide is selected from the group consisting of heparin, dextran sulfate, heparin sulfate, chondroitin sulfate A, chondroitin sulfate D, and chondroitin sulfate E.

6. A method for increasing the hepatocyte growth-stimulating activity of a hepatocyte-growth factor in vivo which comprises combining a sulfated polysaccharide with said hepatocyte-growth factor.

7. The method according to claim 6, wherein the sulfated polysaccharide is glycosaminoglycan.

8. A method for increasing the hepatocyte-growth stimulating activity in vivo of a hepatocyte growth factor which comprises combining with said hepatocyte growth factor, at least one compound selected from the group consisting of heparin, dextran sulfate, heparin sulfate, chondroitin sulfate A, chondroitin sulfate D, and chondroitin sulfate E.

* * * * *